United States Patent
Jennissen et al.

(10) Patent No.: US 6,843,963 B1
(45) Date of Patent: Jan. 18, 2005

(54) FLOW-THROUGH SHEAR ANALYZER FOR BIOLOGICALLY ACTIVE MOLECULES IN LIQUID LAYERS ON SURFACES

(75) Inventors: Herbert Peter Jennissen, Von-der-Vogelweide-Strasse 39, D-45279 Essen (DE); Thomas Zumbrink, Ratingen (DE)

(73) Assignee: Herbert Peter Jennissen, Essen (DE)

( * ) Notice: Subject to any disclaimer, the term of this patent is extended or adjusted under 35 U.S.C. 154(b) by 0 days.

(21) Appl. No.: 09/701,066

(22) PCT Filed: May 25, 1999

(86) PCT No.: PCT/DE99/01529

§ 371 (c)(1),
(2), (4) Date: Nov. 22, 2000

(87) PCT Pub. No.: WO99/61896

PCT Pub. Date: Dec. 2, 1999

(30) Foreign Application Priority Data

May 25, 1998 (DE) .......................... 198 23 301

(51) Int. Cl.[7] .................. G01N 21/47; G01N 21/00; G01N 15/06; G01N 33/00; G01N 33/48
(52) U.S. Cl. .................. 422/82.05; 422/50; 422/55; 422/68.1; 422/81; 422/82; 422/82.07; 422/82.08; 436/8; 436/43; 436/52; 436/53; 436/63; 436/70; 436/164; 73/1.01; 73/1.02; 73/53.01; 73/53.04; 73/53.06; 73/54.02
(58) Field of Search .......................... 422/68.1, 50, 81, 422/82, 55, 82.05, 82.07, 82.08, 82.09, 82.11; 436/8, 43, 52, 53, 63, 70, 164, 165, 166, 174, 178, 180, 167, 171, 172; 73/1.01, 1.02, 53.01, 53.04, 53.06, 54.02

(56) References Cited

U.S. PATENT DOCUMENTS

| 4,028,056 A | * | 6/1977 | Snyder et al. | ............... 436/514 |
| 4,413,505 A | * | 11/1983 | Matson | ....................... 73/61.55 |
| 5,972,710 A | * | 10/1999 | Weigl et al. | .................. 436/34 |
| 6,184,978 B1 | * | 2/2001 | Kasdan et al. | .............. 356/246 |

* cited by examiner

*Primary Examiner*—Jim Warden
*Assistant Examiner*—Brian Sines
(74) *Attorney, Agent, or Firm*—Rutan & Tucker

(57) ABSTRACT

The adsorption rate of proteins from solutions on surfaces in the region of interface layers is often so large that a depletion of the protein in the interface layer results. Due to this, the total reaction becomes transport-dependent, sensitively disrupting the determination of the rate constants. In known TIRF-analysis chambers or bio-sensor systems with a liquid interface layer of ~10 $\mu$m thickness and mass transport coefficients of $10^{-6}$–$10^{-5}$ m/s it has up limitation.

Figure 1:
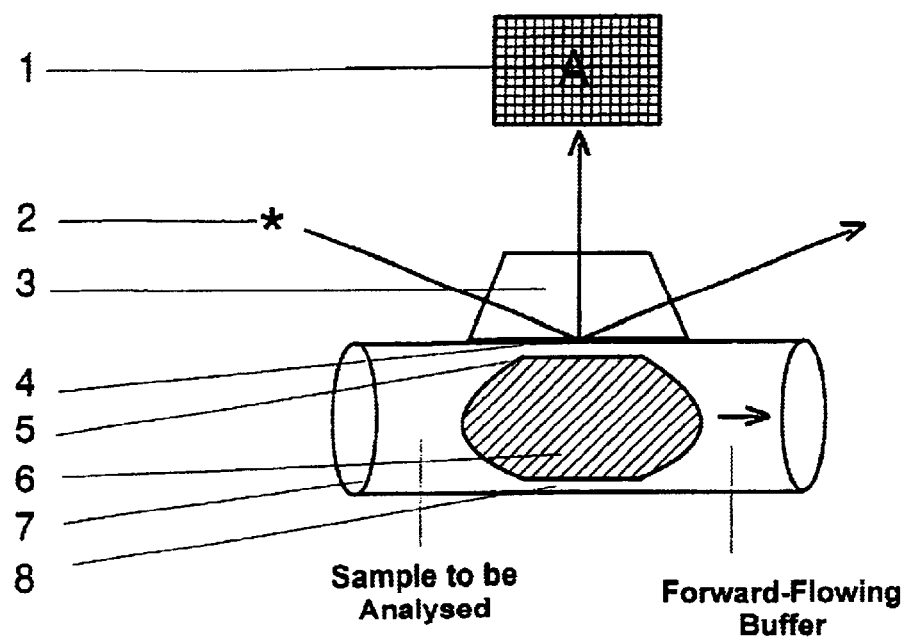

With the help of a TIRF-flow-through shear analyzer in which a certain volume unit of an immiscible fluid, for example an air bubble, is fed into the buffer flow, an ultra-thin liquid layer arises on the surface with a thickness of 100–200 nm, wherein interface surfaces below 10 nm thickness are technically possible.

The new TIRF-flow-through shear analyzer therefore allows the generation of ultra-thin liquid layers while increasing the mass transport coefficients for proteins by 50–100-fold so that the sorption rate constants can be determined without transport limitation.

20 Claims, 6 Drawing Sheets

FLOW-THROUGH SHEAR ANALYZER FOR BIOLOGICALLY ACTIVE MOLECULES IN LIQUID LAYERS ON SURFACES

The present invention relates to a flow-through-shear analyser with means for rapid mixing and for the generation of ultra-thin liquid layers with the features of the main claim for measurement, in particular, of the adsorption-desorption and reaction kinetic properties of biologically active molecules on surfaces as well as methods of determining these properties.

Surfaces arise in heterogeneous systems in which for example multiple phases with pure surfaces meet one another, wherein the individual components are separated by an interface. If one observes the extension of a phase on a surface close to the interface, one speaks of an interface layer. In the enrichment of, for example, proteins in an interface layer on a surface, which enrichment is effected by non-covalent binding forces, one speaks of adsorption (in a depletion, one speaks of desorption) processes which are characterized by sorptive kinetics. In subsequent reactions on the surface in the course of which the protein can go through conformational changes or structural changes (primary structure), can bind with ligands or can be linked with the surface via covalent bonds—processes which are characterized by reaction kinetics, the adsorption reaction is often completed.

The behavior of biologically important molecules, for example of protein molecules, on surfaces is important in the evaluation of processes in biology, biochemistry, in the implementation of biosensors and in the evaluation of biomedicinal materials. Here, the properties of the surfaces in chromatographic methods, in biosensors and the biocompatibility of the implants are dependent on the binding ability of the proteins and their ligands to the surface. In biosensors one can obtain information as to the blood-hormone concentration from the binding of proteohormones to certain surfaces whereas in implants, the deposition of plasma proteins on the foreign material can lead to the developments of thrombosis and to complement activation.

For direct online measurements of the interaction of proteins and their ligands with surfaces, the prior art describes the use of, for example, surface plasmon resonance, interferometry, elipsometry, reflectrometry or preferably total internal reflection fluorescence, TIRF, in which one makes use of the fact that an incident ray of light is totally reflected at an interface layer between an optically denser medium (for example a solid) and an optically less dense medium (for example a liquid) when the angle of incidence is lager than the critical angle for the optically denser medium. At the point of reflection in the optically denser medium, a wave of the same frequency as the frequency of the incident light arises perpendicular to the surface of the denser medium (so-called evanescent wave) and propagates into the less dense medium. The amplitude of the evanescent wave decreases exponentially in the optically less dense medium. The penetration depth of this evanescent wave propagating into the assay solution is dependent on the wavelength and is in general less than 200–300 nm; it is however sufficiently deep to excite fluorophores close to the interface, whereby an excitation of the majority of the proteins located in the solution (bulk solution) is avoided.

When using an excitation wavelength of 290 nm, it is possible to selectively excite the tryptophan chromophore in a protein, which has a fluorescence maximum at 350 nm. On the other hand it is also possible to incorporate an additional fluorophore into the protein by chemical modification, whereby however the danger of conformational changes in the structure of the protein exists.

After mixing of the sample in the sample chamber the measured adsorption rate of the protein on the surface without or at only minimal flow depends on three different steps: 1. the mass transport of the protein in the interface layer between liquid and solid surface, 2. the intrinsic binding rate and 3. the intrinsic dissociation rate. When the binding rate is very low, as is for example the case at very low surface concentrations of binding sites for the protein on the solid, no depletion of the protein in the interface layer will arise and the adsorption rate will depend only on the intrinsic binding rate.

In many cases the binding rate is however greater than the transport rate so that diffusion is not sufficient to maintain the protein concentration in the surface layer at a constant level, rendering the total reaction dependent on mass transport. That means that the adsorption rate is for example strongly dependent on stirring.

The case also arises that the mixing rate of the sample in the receiving volume of the sample chamber is smaller than the transport rate or the binding rate and it therefore becomes rate-determining for the adsorption rate of the protein. Up to now, a simple solution for the reduction of the mixing times, which are 2–8 s in sample chambers of 100–200 $\mu l$ volumes, was not found in the prior art.

Several solution approaches to the measurement of adsorption kinetic data were published in the prior art, and attempt to do justice to mass transport. The mass transport coefficient (Km), which is defined as Km=D/d (D=diffusion constant, d=layer thickness), for a non-stirred layer thickness of 10 $\mu m$ is, for example, for fibrinogen in the best case $2 \times 10^{-6}$ m/s and leads to a marked limiting of transport. If one however wishes to obtain a direct kinetic signal without the disturbing influence of mass transport, one has to reduce the thickness of the non-stirred layer thickness and must do this to such an extent that the adsorption rate becomes independent of the mass transport through the layer. Up to now, no solutions to the latter problem have been proposed in the prior art.

The goal of the invention is to provide a measurement system and a measurement method with which adsorption-desorption or reaction kinetic measurement values for biologically active molecules can be measured without the disruptive influence of mixing as well as of mass transport.

The inventors have surprisingly found that these problems are solved by providing (1) a flow-through shear analyser, with the help of which the adsorption kinetics of biologically active molecules capable of radiation can be measured on surfaces, wherein the flow-through shear analyser comprises a sample chamber block with a sample chamber located therein for receiving an analysis solution or a buffer solution, which sample chamber comprises a sample chamber wall made of a radiation-permeable material, for example a quartz wall, with a supply line for the analysis solution or the buffer solution into the sample chamber and with a removal line for the analysis solution or the buffer solution out of the sample chamber and with a closable injection opening for introducing a sample solution into the supply line on the supply line-side of the sample chamber, means for greatly shortening the mixing time and especially for generating extremely thin liquid layers in the analysis solution or the buffer solution located in the sample chamber so that the rate of adsorption of the molecules capable of radiation on the surface of the radiation-permeable chamber wall is not influenced by the mass transport of the molecules to this interface layer between solution and surface, as well as a radiation analysis unit for the directing and the evaluation of the radiation emitted by the biologically active molecules made of, if required, a radiation source, a radiation conduit and a radiation analyser, and a pump for supplying the buffer solution via the supply line into the sample chamber and, as the case may be, a pump for leading the buffer solution out of the sample chamber via the removal line.

With the help of the analyser according to the invention, it is possible after very short mixing to determine the sorption- and reaction rate constants of biologically active molecules such as proteins and their ligands with respect to surfaces in an extremely thin layer thickness, wherein the surfaces can be modified or coated with the help of chemical or physical methods or a combination of these methods with very diverse inorganic, organic or biological molecules or materials, in order to control the adsorption-desorption or the reaction characteristics of the biologically active molecules with respect to binding affinity or specificity.

According to the invention, by biologically active molecules any type of molecules which in any way demonstrate a biological activity are to be understood, including monomeric or polymeric biomolecules as well as their ligands. Such biologically active compounds can for example be proteins, pharmaceuticals or other chemical or biochemical compounds which are in any way efficacious in a biosystem. It is, however, in any case decisive that the compounds on the surface or in the interface are amenable to detection via signal generating properties. This can for example be the case via elicited changes in the surface-plasmon resonance, the surface interference spectrum, the refractive index, the surface reflection, the rotation of the polarisation plains of the light or preferably via changes in the radiation emitted from the molecules, which radiation is for example generated by exciting a chromophore present in the molecule for example with light or via labelling of the biologically active molecule with a radioactive isotope. In labelling or introducing for example a chromophore into the biologically active molecule, the adsorption characteristics should remain as unchanged as possible relative to the non-labelled condition.

Should preferably, according to the invention, the TIFR-method be used for the analysis of the radiation emitted from the biologically active molecules, the radiation analysis unit comprises for example an optical unit made of a light source which delivers a monochromatic light beam, a radiation conduit, for example an optical prism and a radiation analyser, for example an emission monochrometer coupled to an evaluation unit, wherein the prism and the light source are arranged with respect to each other in such a way the light beam leaving the light source impinges upon the interface layer between the quartz plates and the solution via the prism which is arranged on the light-permeable quartz plate in an optically coupled manner, in an angle greater than the critical angle for the denser medium, and the fluorescence light formed, which fluorescence light is generated at the interface layer between the quartz plate and the sample fluid in the sample chamber and emerges essentially perpendicularly to the surface of the quartz plate, is directed via an optical system into the emission monochrometer.

In order to achieve the desired thickness of the thin layer, means for generating shear forces and gap pressures are provided according to the invention, which means act inside the sample chamber on the surface of the quartz plate. In this way, these shear forces can be mechanically generated according to the invention. In the simplest case, the shear forces can be generated by a volume flow by the chamber or by the rotation of a cylindrical rotor in the immediate vicinity of the measurement surface. Shear rates generated in this way are typically on the order of $10^4$–$10^5$ s$^{-1}$, lead to liquid layers of 5–15 μm thickness and promote the implementation of the means according to the invention for the generation of ultra-thin layers as well as the further movement of the layers generated.

The decisive reduction of the layer thickness under 5 μm is made possible according to the invention in that, by means of an apparatus arranged on the supply line-side, volume units on the order of 10–100%, preferably 50–75% of the chamber volume, which volume units are of a fluid which is immiscible in the chamber solution, are fed in volume flow segments of preferably identical volume into the chamber solution, which volume units serve as a means of greatly reducing the liquid volumes in the measurement cell and the liquid layer on the measurement surface. The chamber solution can be a hydrophilic aqueous or a hydrophobic organic liquid, wherein the immiscible fluid is of such a nature as to be, in the first case, immiscible with the hydrophilic liquid and, in the second case, immiscible with the hydrophobic liquid. The chamber solution is preferably a buffer solution of a hydrophillic aqueous type. Preferably, the arrangement takes place such that a volume unit of the previously mentioned fluid is introduced immediately prior to the addition of an analysis solution into the buffer solution fed through the sample chamber and reduces the chamber volume and, therefore, the mixing time by displacing the liquid volume, rinses the sample chamber and, in the course of this, the gap pressure between fluid and sample chamber wall generates an extremely this liquid layer of between 10 and 300 nm which no longer represents a measurable transport barrier, since the mass transport coefficient for fibrinogen increases by multiple orders of magnitude from $10^{-4}$ to $10^{-2}$ m/s.

The fluid introduced into the buffer solution can for example be a gas or a liquid which is immiscible in the buffer solution. The use of gas, in the simplest case of air, is preferable. In using gas as the immiscible fluid, depending on flow conditions in the supply line, a single gas bubble can be ruptured into a series of smaller gas bubbles as in a "chain of pearls" upon introduction into the supply line. Furthermore, it is also possible in using gas as the immiscible fluid to reduce the layer thickness between the gas bubble and the sample chamber wall in the sample chamber by increasing the pressure with which the gas is introduced into the supply line. Here the flow-through shear analyser according to the invention is preferably formed as a closed system, i.e. an elevated pressure relative to the external pressure is maintained in the pipe system of the analyser.

Supplying of the fluid on the supply line-side into the supply line to the sample chamber can for example take place via a two-way valve comprising a respective connection for supplying of the buffer solution and the fluid, and for the removal of the volume flow formed. The supply of the fluid can take place continually or discontinuously, whereby for the latter possibility, for example, one can switch back and forth via the position of the two-way valve between the supply of the buffer solution and the fluid.

In the simplest embodiment of the shear analyser a closed system exists and, in the sample chamber, a flow-through cuvette whose cross-section perpendicular to the flow direction is rectangular or circular, which flow-through cuvette is for example set into a sample chamber block and on the wall portion of which is arranged the radiation analysis unit, for example the optical unit for directing and measuring the radiation emitted from the molecules. The flow-through volume can reach values of 1–1000 ml/hour, preferably 150–200 ml/hour with a chamber volume of 100–200 µl, whereby shear rates on the order of $10^4$ $s^{-1}$ or above can arise. On the supply line-side, a defined volume unit of an immiscible fluid is supplied prior to the sample to be analysed as a means of reducing the fluid in the chamber and therefore the mixing time, but in particular as a means of generating an extremely thin liquid layer. A continuous flow-through is preferred while generating a constant shear rate (preferably 500–1000 $s^{-1}$) in one direction by moving the ultra-thin liquid layer through the liquid flow into the TIRF-measurement area, whereby the temperature is held constant. The biologically active molecules are adsorbed in the region of the solid/liquid interface on the quartz glass wall of the sample chamber and are detected by the optical unit on the analyser.

If very rapid relaxation kinetic experiments are to be carried out, a volume unit of the immiscible fluid is fed in a continual flow at high flow-through rate into the sample chamber before the analysis solution. If the immiscible fluid volume and, therefore, the extremely thin liquid layer is preferably in the region of the measurement field, then the liquid flow is momentarily stopped (so-called "stopped flow" or "stopped flow concentration jump" method), so that the interaction of the biologically active molecules with the surface in the absence of shear forces can be recorded at a defined location of the quartz glass wall by the optical system. In the course of such an experiment it can become necessary to reverse the fluid flow in its direction in order to, for example, subject other areas of the extremely thin liquid layer, of the interface or of the fluid phase additionally or at another temperature to a measurement in the same experiment. The temperature can also be changed by jumping in the absence of flow in order to perform "stopped-flow temperature jump" experiments. In the flow-through shear analyser according to the invention, the biologically active molecules can be located in four regions following the introduction of immiscible fluid. (1) In the solid/liquid interface, (2) in the liquid/fluid interface, (3) in the liquid bulk phase or (4) the fluid bulk phase. In the area of the ultra-thin liquid layer generated by the previously mentioned fluid, concentration changes of the biologically active molecules in all four regions were accessible to a measurement given a sufficient penetration depth of the evanescent wave.

In an another preferred embodiment of an open system, the analyser according to the invention is made in such a way that the means for generating the extremely thin liquid layers are made by forming the sample chamber in the shape of a cylindrical rheometer chamber for receiving the analysis or the buffer solution, the one end of which is sealed closed with a light-permeable quartz plate in which a cylindrical rotor, preferably made of a light-permeable material, is rotatably mounted, the outer diameter of which is adapted to the inner diameter of the rheometer chamber, wherein the cylindrical rotor on the side directed towards the quartz plate is made to be conical and touches the quartz with the point of the cone laying in the rotational axis of the rotor; and which comprises one supply line and one removal line for the buffer solution into the sample chamber which is made of rheometer chamber inner walls, a rotor cone and a light-permeable quartz plate, and a motor for driving the rotor is provided.

This embodiment of the analyser according to the invention has as an essential component the analyser unit and the optical unit which is coupled to the analyser unit. Here, the analyser unit comprises a chamber block with a cylindrical rheometer chamber located therein, in which a rotor made of a light-permeable material such as for example polymethylmethacrylate is rotatably mounted, whereby the outer diameter of the rotor is adapted to the inner diameter of the cylindrical analyser chamber.

The end of the analyser chamber is closed by a light-permeable solid plate, for example a quartz glass plate, the surface of which can be chemically or physically modified, wherein the rotor on the side directed towards the light-permeable quartz plate is formed to be conical, and the rotor touches the light-permeable quartz plate with the point of the cone and forms the actual analyser chamber. The angle of the point of the cone to the rotational axis (cone inclination/rotational axis) is approximately 85° to 89.9°, preferably 89°, so that a sample chamber with a triangular radial cross section existing around the rotational axis of the rotor is formed, whereby the triangular angle at the point of the cone is about 0.1° to 5°, preferably 1°.

The diameter of the rheometer chamber or of the rotor, in general about 2–4 cm, is determined as dependent on the triangular angle previously mentioned so as to yield a sample chamber volume of 10 up to 1000 µl, preferably 50 to 150, especially preferred 100–120 µl. A buffer solution is fed into the sample chamber via a supply line and is removed via a removal line which are preferably arranged in the quartz plate. A shear force field for generating shear rates via the buffer solution in the sample chamber is generated by the rotating cone on the quartz plate on which the protein is to be adsorbed, and after introduction of the analysis-solution containing the protein, the adsorption of the protein onto the surface is correspondingly investigated as dependent on the rotational speed of the rotor.

Here, the chamber is preferably formed such that simultaneously, i.e. during rotation of the rotor, the flow-through volume (chamber with 1° angle) can assume a value of between 1 to 500 ml per hour, preferably 150 ml per hour. This volume flow-through additionally generates a significant shear rate on the order of $10^4$ $s^{-1}$ so that a system arises in which the total shear rate can be viewed as the sum of the shear rate of the flow-through and the shear rate of the cone rotation.

Using the apparatus according to the invention and using the method using the apparatus, it is possible to determine the protein adsorption in the solid/liquid interface on the quartz glass plate under exactly defined external shear forces and layer thicknesses. The apparatus can also be used, for example, to simulate the shear conditions in blood flow in vivo during protein absorption, and to analyse the shearing induced by the flow in adsorption chromatography columns for protein separations.

In a preferred embodiment, the supply line and the removal line of the buffer solution in the sample chamber are arranged in line with the point of the cone on the quartz plate, and it is further preferred that the supply line is arranged close to the point of the cone. In this way the solution to be studied can be introduced at the point of the sample chamber at which the latter has the least axial expansion (so that during the adsorption of the proteins onto the possibly modified surface of the quartz plate the layer to be penetrated exhibits as thin-a thickness as possible) and in this way, as thin a thickness as possible must be penetrated by the proteins for the adsorption of the proteins on the possibly modified quartz plate.

The injection opening for introducing the sample solution is preferably located in the supply line of the buffer solution into the sample chamber, especially preferred in the supply line close to the quartz plate at the point where the quartz plate and the supply line are connected to one another. In introducing the sample solution containing the proteins to be studied, preferably close to the rotational axis of the rotor via the injection opening by means of a pump and a supply line into the sample chamber, the sample solution is diluted by the buffer solution, being moved radially and tangentially is outward, and the proteins contained in the solution therefore come into contact with the possibly modified quartz surface and are adsorbed.

Of about the same importance as the supply is the removal of the buffer solution from the chamber. The removal line of the chamber can be connected to a suction pump which actively sucks the liquid out of the chamber, a method which is preferably applied in open systems. In this way extremely high flow-through-races of up to 500 ml/hour are possible.

Surprisingly, the inventors determined that the sensitivity of the method can be definitively enhanced if, immediately prior to the solution to be studied, a volume unit of 10 to 100% of the chamber volume, preferably 50–75% of the chamber volume of a fluid which is immiscible with the solution to be studied is introduced into the rheometer chamber. This fluid can be composed of a liquid which is immiscible in the solution, to be studied or a gas bubble, which itself can be composed of a non-noble gas or a noble gas or of both one after the other. This procedure is performed in order to first rinse the adsorption surface on the quartz plate of foreign matter, to reduce the effective liquid volume in the chamber within a very short time to 10–30% for a very rapid mixing within 0.5–1 s, but mainly to generate an extremely thin liquid layer of 10–300 nm thickness on the quartz glass surface.

Here it is especially preferred that the introduction of the fluid into the sample chamber takes place in the form of an air bubble which is introduced immediately prior to the sample solution into the sample chamber, and which first almost completely displaces the buffer solution present in the sample chamber, so that a direct wetting of the adsorption surface on the quartz plate with the protein-containing sample solution to be studied is made possible. Here, the size of the dead volume or of the air bubble is up to 1000 $\mu$l, preferably up to 150 $\mu$l and especially preferably up to 75 $\mu$l. The air bubble is then immediately removed by the sucking apparatus.

In another application the rotation of the rotor and the liquid flow can be maintained, preferably if the air bubble and, therefore, the extremely thin liquid layer is located in the measurement field of the quartz glass plate.

The present invention is therefore directed to a method of analyzing a liquid for a component contained in the liquid, which method is characterized in that the liquid flow to be analysed through a sample analysis chamber, which liquid flow is to be studied for the component(s), is subdivided by volume units which are immiscible in the liquid before introduction into the sample analysis chamber, and in this form enters into the sample chamber. In this way, the liquid flow can be subdivided into volume flow segments by supplying volume units of a liquid which is immiscible in the liquid or air bubbles or both, so that a repeated generation of extremely thin liquid layers on the surface is effected. That is necessary, for example, with very slow kinetics in a low concentration range. This is achieved in the most simple case by directing the liquid flow via a two-way valve with one lead each for the liquid flow of the buffer solution and the immiscible fluid and with a common removal line in the direction of the sample analysis chamber, wherein during the analysis the liquid flow in the sample analysis chamber is intermittently switched in intervals between both of the supply positions on the two-way valve. To this end the two-way valve of both the liquid flow and the immiscible liquid or air is supplied with the help of pumps.

When biologically active molecules such as for instance proteins are contained in the liquid to be studied, the adsorbed proteins can be optically detected with the help of a fluorescence spectrophotometer with an excitation wavelength of 290 nm and an emission wavelength of 350 nm. In addition, a prism is mounted on the quartz plate, which prism is optically coupled with the quartz plate, for example by means of a medium of the same refractive index, for example glycerine. In addition, a monochromatic light beam from a xenon lamp is generated which, directed via an excitation monochrometer, impinges upon the prism at a nearly right angle and the evanescent wave interacts with the proteins adsorbed on the solid/liquid interface and excites the tryptophan therein, serving here as fluorophore, to emission of fluorescent light. This fluorescent light emerges in a direction parallel to the axis of rotation of the rotor perpendicular to the quartz plate and is directed via an optical system of mirrors and lenses into an emission monochrometer, which itself is connected to a photomultiplier for the determination of the light intensity.

In a second preferred application it is possible that, using a non-adsorbing quartz plate, the evanescent wave passes through the solid/liquid (liquid/quartz plate) interface unchanged and, on the other side of the liquid film, penetrates into the liquid/gas bubble phase interface layer in order to determine, in a time-resolved fashion, the fluorescence of the biologically active molecules enriched in the interface or adsorbed at the interface, for example for the production of floatation- or foam-separation methods for the fractionation of biological materials.

In a third preferred type of application the present invention is directed to the determination of the thickness of the extremely thin liquid film itself with the help of the evanescent wave. To this end, the flow-through cell is, flowed-through with a highly fluorescent solution, for example 4.5 mM hydroxytryptophan, which is trapped by two air bubbles in a tube and which then emerges. If the air bubble passes the measuring field and if the thickness of the liquid layer is larger than the penetration depth of the evanescent wave, then there will be no measurable change in the fluorescent signal. If on the other hand the thickness of the ultra-thin liquid layer is smaller than the penetration depth of the evanescent wave, then the evanescent wave will completely penetrate the liquid film, in other words it will enter at the solid/liquid interface and will emerge again at the liquid/air interface, to enter into non-fluorescing air in the interior of the bubble, which leads to an immediate reduction of the fluorescence signal. Since the penetration depth of the evanescent wave is known, the layer thickness of the liquid layer can be determined. Since furthermore the penetration depth of the evanescent wave depends on the wavelength of the light, any desired penetration depth for any desired layer thickness can be generated. Layer thickness determinations of this type are of great importance for the elucidation of mass transport coefficients of biologically active molecules in interface layers for kinetic or relaxation kinetic measurements, in particular for bio-sensor, systems. Furthermore, the production of ultra-thin layers in material coating methods in chemical industry could be monitored with such a method for determining the layer thickness.

The fluorescence signal is measured (in measurement signals per second) CPS relative to the fluorescence of the buffer control. The supply and removal lines can, of course, also be arranged in the outer wall of the rheometer chamber, whereby however the previously described arrangement of the supply and removal line in the quartz plate in line with the rotational axis of the rotor or the point of the cone represents the most advantageous embodiment.

FIG. 1 shows a form of the flow-through shear analyser simplified to the most essential elements, and composed on the one hand of a sample chamber (7) similar to a flow-through cuvette, which sample chamber (7) has a circular cross section in the flow direction. The optical unit is located on the upper portion of the wall and is composed of a light source (2), an optically coupled prism (3), and a fluorescence light analyser (1) for directing and measuring the light radiation emitted from the molecules. A defined volume unit of an immiscible fluid (6), preferably an air bubble, has been fed to the left on the side of the supply line behind the forwardly flowing buffer and before the sample to be analysed. Between the fluid and the chamber wall an extremely thin (100–200 nm thick) liquid film (8) is generated due to the gap pressure, which liquid film (8) forms a liquid/solid (4) and a liquid/fluid (5) interface. In such a closed flow-through shear analyser system, a liquid flow normally occurs in the direction of the arrow, whereby, if needed, a halting of the flow (stopped flow) or a reversal of flow can take place. At the same time the hydrostatic pressure in the chamber can be raised or lowered to change the gap pressure. Furthermore, the partial pressure in the air bubble can be varied, for example by raising the temperature, to change the gap pressure. The evanescent wave generated in the reflection point of the light beam (2) penetrates the ultra-thin liquid layer downwardly and perpendicular to the direction of flow and allows the analysis of biologically active molecules according to border conditions in the liquid/solid (4) interface, the liquid/fluid (5) interface or in the bulk phase of the ultra-thin liquid layer (6) or in a volatile molecule in the gas cavity itself.

Figure 2:
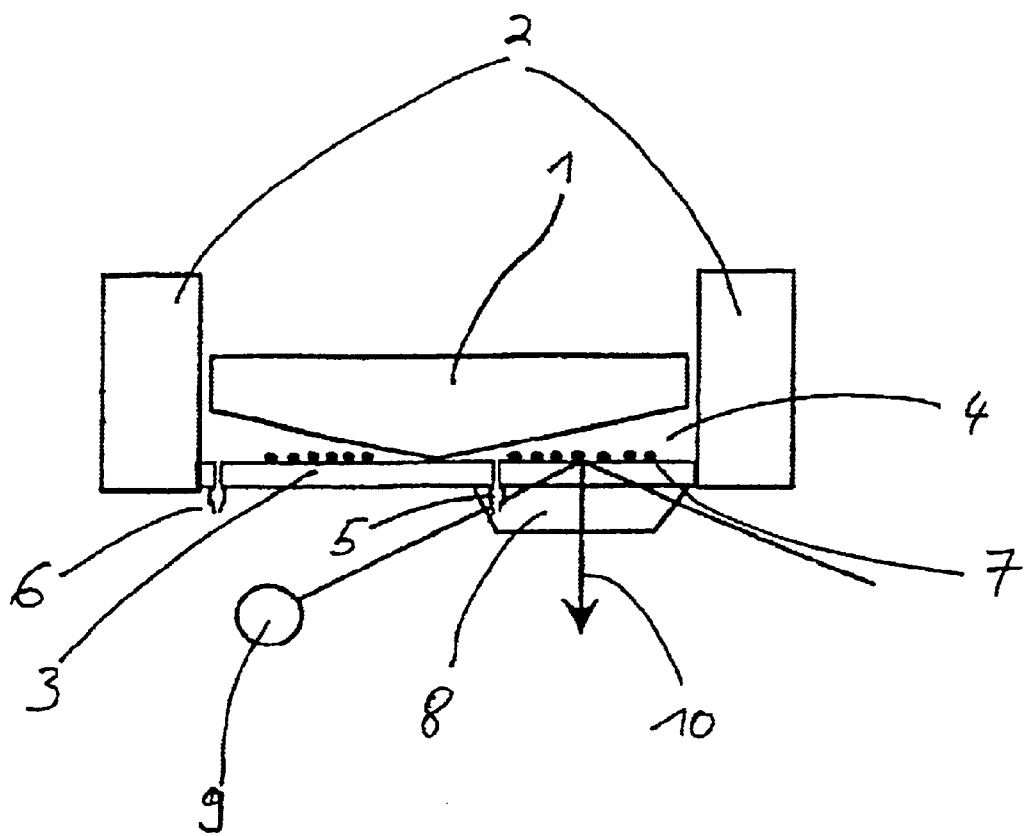
Figure 3:
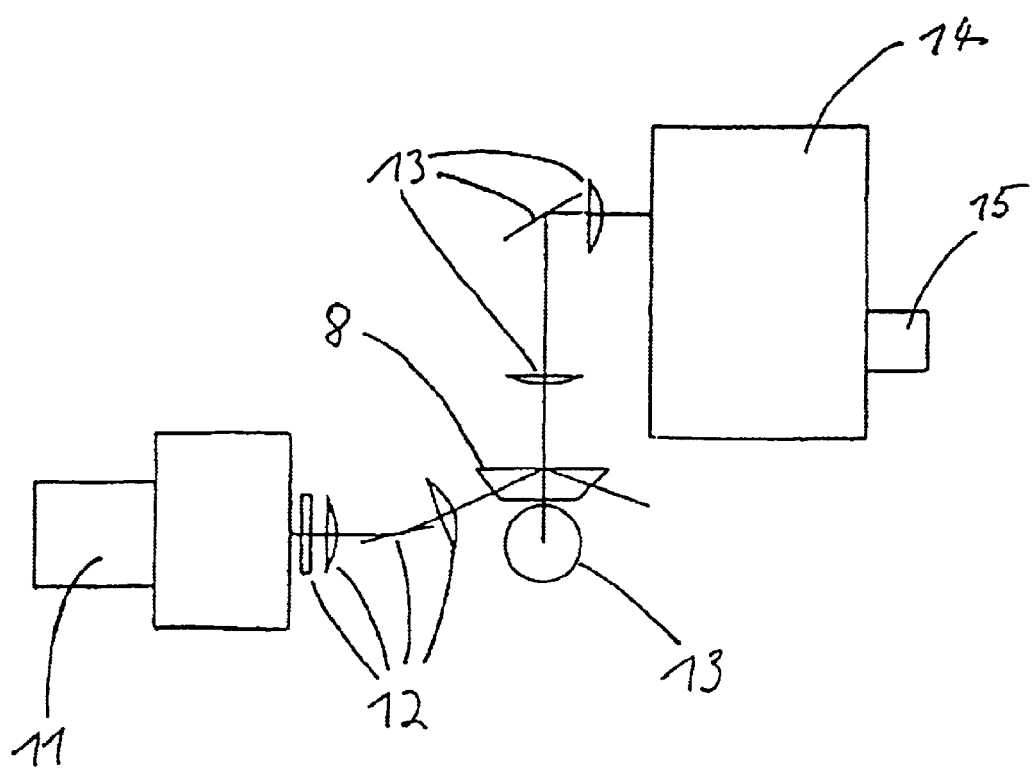

The following describes a preferred embodiment of the rheometer according to the invention with reference to the included FIGS. 2 and 3.

Here, FIG. 2 shows a schematic longitudinal cross section through an analyser with a rheometer-unit according to the invention at the height of the rotational axis of the rotor; and FIG. 3 shows the schematic construction of the optical unit used.

As shown in FIG. 2 in a longitudinal cross section through the rheometer unit according to the invention, the rotatable rotor (1) is mounted in a rotatable fashion inside in the rotor chamber walls (2), shown schematically here. The rotor touches the quartz plate (3) with the point, and the quartz plate (3) is held to be tightly sealed between the side walls (2) of the rotor chamber. The supply line (5) enters into the sample chamber (4) close to the point of the cone touching the quartz plate (3), and the liquid supplied via the supply line (5) is then actively removed from the sample chamber by sucking. During rotation of the rotatably mounted rotor, which is driven by the motor (not shown), shear forces act on the liquid film adhering to the side of the quartz plate facing the sample chamber, in which liquid film the proteins, indicated in FIG. 2 as black dots, are contained, whereby the thickness of the liquid layer is reduced by the shear forces with increasing rotational speed.

A prism (8) is mounted on the side of the quartz plate (3) facing away from the sample chamber in an optically coupled fashion as close as possible to the supply line (5) of the buffer solution, or as close as possible to the injection opening (not shown in the drawing) for the sample solution to be studied, which injection opening is arranged in the supply line of the buffer solution. The light beam emerging from the light generating unit (9), itself shown only schematically here, is directed via the prism to the adsorbed proteins and excites the tryptophan fluorophore present in the proteins to generate a fluorescent light (10) which emerges perpendicularly in the direction of the prism parallel to the axis of, the rotation of the rotor (5), and which is directed in the direction of the emission monochrometer coupled to an analysis unit, themselves not shown in FIG. 2.

In FIG. 3 the light path of the monochromatic light generated is shown in more detail. Here, the light generated by the xenon lamp (11) is first transformed into monochromatic light, is directed via optical elements such as slit gratings, lenses and mirrors (12) onto the prism (8), and the fluorescence light beam (10) emitted from the sample is directed via lenses and mirrors (13) into the emission monochrometer (14), which itself is connected with a photomultiplier, and whose signals are evaluated in a 15A calculation unit (15) connected thereto.

Figure 4:
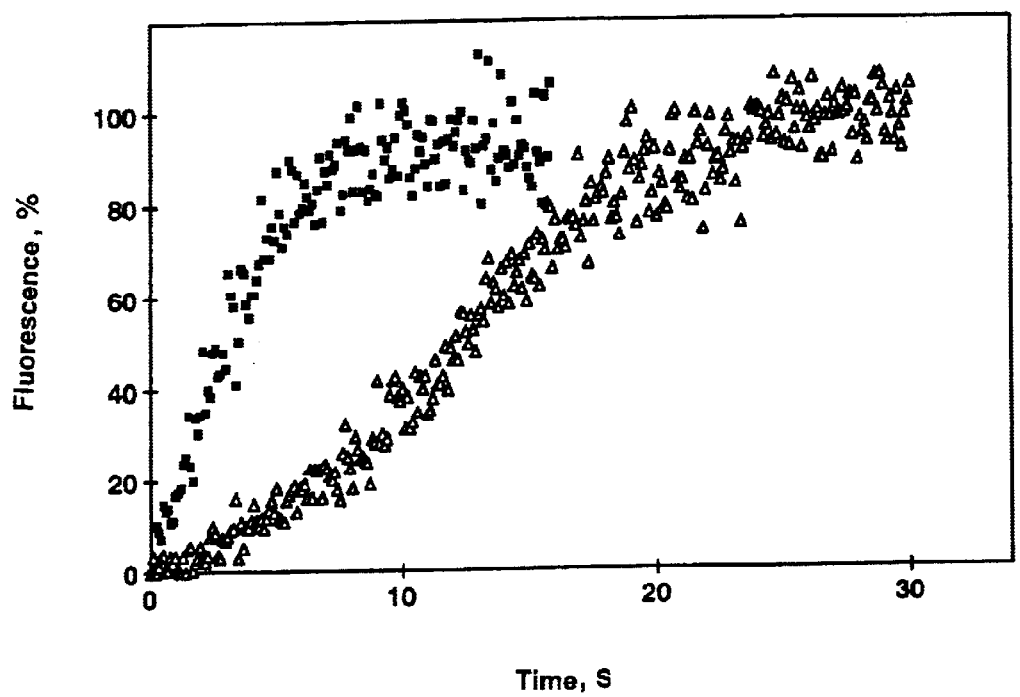
Figure 5:
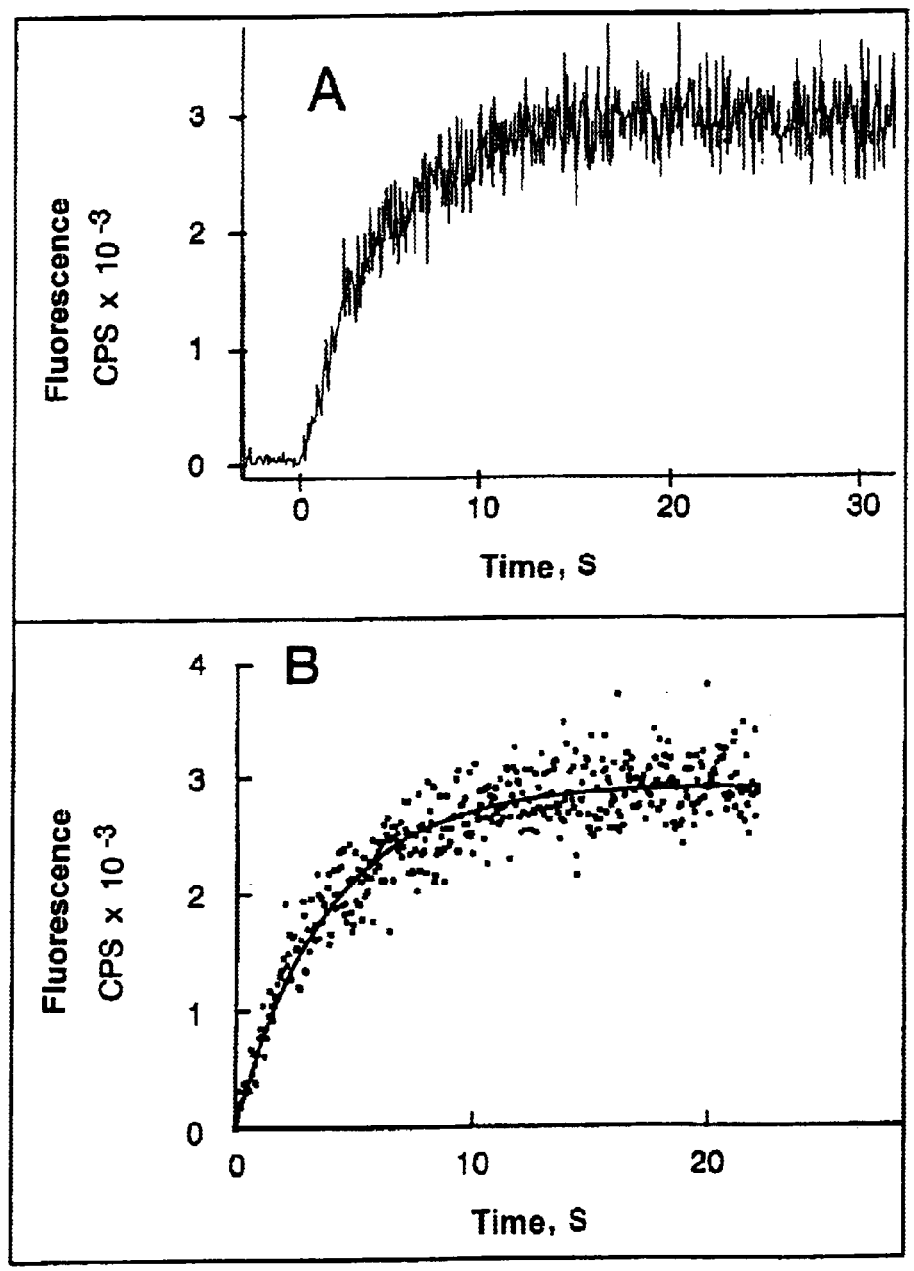

By using the rheometer according to the invention as is shown in FIGS. 2 and 3, the adsorption kinetic properties were measured, by way of example, for fibrinogen, and the results obtained are shown in FIGS. 4 and 5 at a constant temperature of 23° C.

Here, FIG. 4 shows the comparison of the adsorption rates of fibrinogen onto quartz glass, wherein an air bubble of 75 $\mu$l (solid squares), or no air bubble (open triangles) was injected into a chamber of 120 ml prior to the solution to be studied. The protein concentration here was 100 $\mu$g/ml, the flow-through rate was 150 ml/hour and the shear rate of the rheometer was 7200 s$^{-1}$. As can be taken from diagram 1, the half life time of the adsorption decreases from 12.7 seconds (without air bubble) to 2.6 seconds (with air bubble) by the preinjection of an air bubble. Furthermore, the sigmoidicity of the curve disappears in favor of an exponential function. The uncorrected 100% values were 2300 cps without and 2000 cps with air bubble.

FIG. 5 shows the exponential adsorption kinetics of fibrinogen onto quartz glass as measured by the method of TIRF rheometry with preinjection of an air bubble. In this measurement, the protein concentration, held constant in flow-through, was 188 $\mu$g/ml, the flow-through rate was 150 ml/hour and the shear rate of the rheometer was 720 s$^{-1}$. The original online recording of the kinetics is depicted in the upper diagram A. Non-linear fitting of the 443 experimental points to the exponential function [(F=$F_{max}$ (1−e$^{*k_{obs} \cdot t}$), wherein F represents the fluorescence in cps, $F_{max}$ represents the maximal fluorescence in cps, $k_{obs}$ represents the observed rate constant as the increase of the exponential function and t represents the time], yielded the values $k_{obs}$=0.261+0.006 s$^{-1}$, P-value of the residuals=0.138 and $r^2$=0.90. If the $k_{obs}$-values measured with various fibrinogen concentrations ($C_0$) are applied as a function of the concentration $C_0$ according to the equation $k_{obs}$=k$_{+1}$ $C_0$+k$_{-1}$, a line is obtained which can be used to simultaneously determine the desorption rate constant (k$_{-1}$=0.082 s$^{-1}$) as the intercept with the ordinate and the adsorption rate constant (k$_{+1}$=3.5× 10$^5$ M$^{-1}$s$^{-1}$) as the slope of the line. Independent determinations of the desorption rates of fibrinogen using air bubble techniques allowed the elucidation of additional rate constants for the desorption (k$_{-2}$=2×10$^{-4}$ s$^{-1}$, k$_{-3}$=5.8×10$^{-6}$ s$^{-1}$) which could be correlated to reaction kinetics between the adsorbed molecules on the surface, conformational changes (k$_s$−0.1 s$^{-1}$) or to reactions with ligands of the adsorbed proteins. In the simplest case the binding of a second fibrinogen molecule dissolved in buffer to the first fibrinogen molecule adsorbed on the surface represents one such ligand, whereby a double or multiple protein layer on the surface is known to arise. Yet such ligands can also be represented by ions, organic molecules or cofactors and can lead to changed rate constants.

Figure 6:
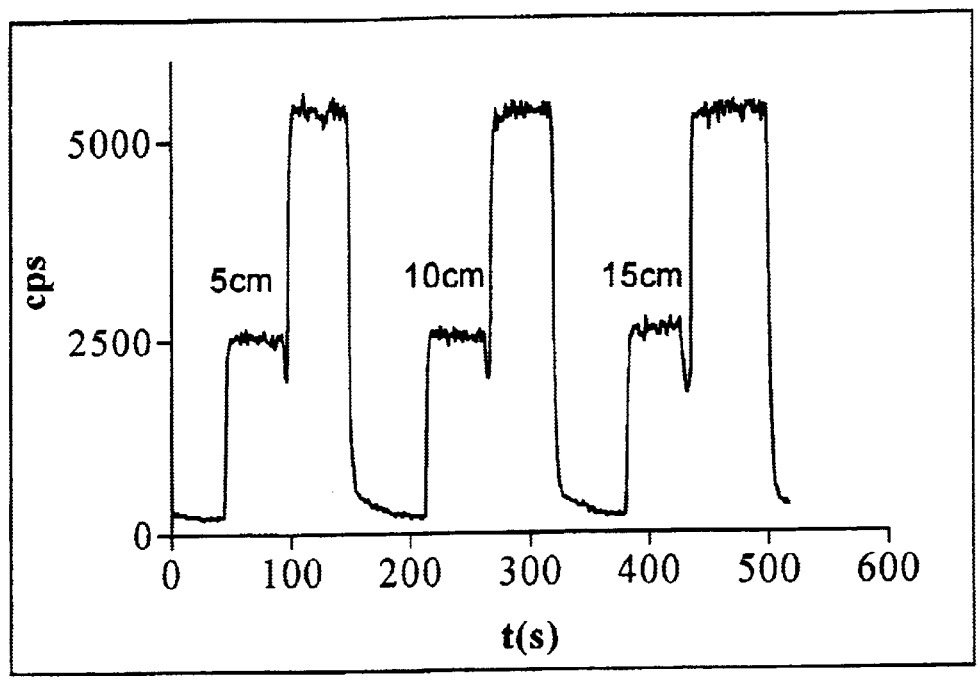

The embodiment of the rheometer according to the invention in FIG. 6 demonstrates the measurement of the penetration of the evanescent light wave into and through the ultra-thin liquid layer into the gas cavity of the air bubble at a constant temperature of 25° C. A hydroxytryptophan standard of concentration 0.22 mM (first increase of about 200 cps to 2500 cps) is separately fed by an air bubble of a second following concentration of 0.68 mM (second increase to 5200 cps) through the measurement chamber and then purged separately through water (decrease from 5200 cps to 200 cps). The penetration of the evanescent wave into the air cavity of the bubble is visible as a steep decline of the fluorescence ("nose") of 2500 cps from the level immediately preceding the increase to 5200 cps. Fed at a flow-through rate of 145 ml/h through the rheometer chamber (chamber volume: 120 $\mu$l) and at an air bubble size of 5, 10, 15 cm in a silicon tube (diameter 1.3 mm), this represents an approximate air volume of 75 $\mu$l, 150 $\mu$l and 225 $\mu$l. The surface of the "nose" increases with the size of the air bubble, which represents the longer persistence time of the evanescent wave in the bubble. Since the evanescent wave had a penetration depth of ~250 to 300 nm under the experimental condition used, the liquid film penetrated must have a layer thickness of less than 300 nm.

What is claimed is:

1. An analyzer, comprising:
   a sample chamber having a measuring surface and a plurality of walls, wherein at least one of the plurality of walls is radiation permeable;
   a supply line fluidly coupled to the sample chamber and supplying a mixture of a chamber solution and a fluid immiscible with the chamber solution to the sample chamber;
   wherein the sample chamber is configured such that a film of chamber solution is formed between the measuring surface and the immiscible fluid when the mixture is in the sample chamber; and
   an optical detector coupled to the sample chamber and configured to detect an analyte signal from the film.

2. The analyzer of claim 1, wherein the sample chamber is disposed within a sample chamber block, and wherein the supply line further comprises a closable injection opening.

3. The analyzer of claim 2 further comprising at least one of a radiation source, a radiation conduit, and a radiation analyzer.

4. The analyzer of claim 3 further comprising a first pump fluidly coupled to the supply line, wherein the first pump supplies the chamber solution to the chamber, and further comprising a second pump fluidly coupled to a removal line that is fluidly coupled to the sample chamber.

5. The analyzer of claim 3 wherein the radiation source comprises a light source that produces a monochromatic light beam, wherein the radiation conduit comprises an optical prism, and wherein the radiation analyzer comprises an emission monochrometer.

6. The analyzer of claim 5 wherein the radiation conduit and the light source are configured such that a light beam from the light source impinges upon the measuring surface at an angle larger a critical angle, and wherein a fluorescence light generated at the measuring surface is directed via an optical system to the radiation analyzer.

7. The analyzer of claim 1, wherein the chamber solution comprises at least one of a hydrophilic liquid and a hydrophobic liquid.

8. The analyzer of claim 1, wherein the fluid that is immiscible with the chamber solution is selected from the group consisting of a gas and a liquid.

9. The analyzer of claim 1, wherein the chamber solution comprises a buffer, and wherein the fluid that is immiscible with the chamber solution comprises a gas.

10. The analyzer of claim 1, wherein the sample chamber comprises a radiation-permeable flow-through cuvette that has a triangular or circular cross section perpendicular to a flow direction of the chamber solution.

11. The analyzer of claim 10, wherein at least one radiation permeable wall comprises quartz glass.

12. The analyzer of claim 10, wherein the at least one radiation permeable wall further comprises a coating that promotes specific binding of the signal-generating molecule to the radiation permeable wall.

13. The analyzer of claim 1, wherein the analyte comprises a biologically active molecule.

14. The analyzer of claim 13, wherein the biologically active molecule comprises a protein, and wherein the biologically active molecule reacts with a ligand.

15. The analyzer of claim 1, wherein the sample chamber is cylindrical, wherein a light-permeable rotor is rotatably disposed within the sample chamber, wherein the sample chamber is closed on one end by a light-permeable quartz plate, and wherein the analyzer further comprises a motor that actuates the rotor.

16. The analyzer of claim 15 further comprising a removal line, wherein the rotor has a rotational axis, and wherein the supply line and the removal line are arranged diametrical to the rotational axis.

17. The analyzer of claim 16 wherein the supply line and the removal line are at least partially disposed within the quartz plate.

18. The analyzer of claim 15 wherein the supply line further comprises a closable injection opening.

19. The analyzer of claim 16 wherein the rotor has a cone shaped surface, and wherein the rotational axis and a tangent to the cone-shaped surface form an angle between 58 degrees and 89.9 degrees.

20. A method of analyzing a component in a liquid, comprising:
   providing a sample analysis chamber comprising a measuring surface;
   feeding a mixture of the liquid and a fluid that is immiscible with the liquid into the sample analysis chamber such that a film is formed from the liquid, wherein the film is disposed between the measuring surface and the immiscible fluid when the mixture is in the sample chamber; and
   optically detecting an analyte signal from the film.

* * * * *